US010504353B2

(12) United States Patent
Wiggermann et al.

(10) Patent No.: US 10,504,353 B2
(45) Date of Patent: Dec. 10, 2019

(54) CUSTOMIZED BED EXIT WARNINGS TO MODIFY PATIENT BEHAVIOR

(71) Applicant: Hill-Rom Services, Inc., Batesville, IN (US)

(72) Inventors: Neal Wiggermann, Batesville, IN (US); Robert M Zerhusen, Cincinnati, OH (US); Richard H Heimbrock, Cincinnati, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 525 days.

(21) Appl. No.: 15/212,669

(22) Filed: Jul. 18, 2016

(65) Prior Publication Data
US 2017/0032650 A1    Feb. 2, 2017

Related U.S. Application Data

(60) Provisional application No. 62/197,294, filed on Jul. 27, 2015.

(51) Int. Cl.
| | |
|---|---|
| *A61G 7/018* | (2006.01) |
| *G08B 21/04* | (2006.01) |
| *A61B 5/00* | (2006.01) |
| *A61B 5/11* | (2006.01) |
| *G08B 21/22* | (2006.01) |
| *A61G 7/015* | (2006.01) |
| *A61G 7/05* | (2006.01) |

(52) U.S. Cl.
CPC ........ *G08B 21/0461* (2013.01); *A61B 5/1115* (2013.01); *A61B 5/741* (2013.01); *A61B 5/742* (2013.01); *A61G 7/015* (2013.01); *A61G 7/018* (2013.01); *A61G 7/05* (2013.01); *A61G 7/0527* (2016.11); *G08B 21/22* (2013.01); *A61G 2203/10* (2013.01); *A61G 2203/44* (2013.01)

(58) Field of Classification Search
CPC ....................................................... A61G 7/018
USPC ....................................................... 5/600, 424
See application file for complete search history.

(56) References Cited

U.S. PATENT DOCUMENTS

| | | | |
|---|---|---|---|
| 4,179,692 | A | 12/1979 | Vance |
| 4,295,133 | A | 10/1981 | Vance |
| 4,484,043 | A | 11/1984 | Musick et al. |
| 4,565,910 | A | 1/1986 | Musick et al. |
| 4,700,180 | A | 10/1987 | Vance et al. |
| 4,792,990 | A | 12/1988 | Beyers et al. |
| 4,803,625 | A | 2/1989 | Fu et al. |
| 4,907,845 | A | 3/1990 | Wood |
| 5,224,496 | A | 7/1993 | Palmer et al. |
| D361,462 | S | 8/1995 | Newham |
| 5,519,380 | A | 5/1996 | Edwards et al. |
| 5,554,835 | A | 9/1996 | Newham |
| 5,561,412 | A | 10/1996 | Novak et al. |

(Continued)

FOREIGN PATENT DOCUMENTS

| | | |
|---|---|---|
| EP | 191906 A2 | 1/1991 |
| WO | 2004082477 A1 | 9/2004 |

*Primary Examiner* — Fredrick C Conley
(74) *Attorney, Agent, or Firm* — Barnes & Thornburg LLP (57) ABSTRACT

A patient support apparatus includes a frame, a support surface, and a sensor. The frame cooperates with the support surface to support a patient. The sensor is coupled to one of the frame and the support surface and is configured to provide an input signal indicative of a characteristic associated with the patient.

18 Claims, 8 Drawing Sheets

(56) References Cited

U.S. PATENT DOCUMENTS

| | | |
|---|---|---|
| 5,600,108 A | 2/1997 | Newham |
| 5,623,760 A | 4/1997 | Newham |
| 5,633,627 A | 5/1997 | Newham |
| 5,640,145 A | 6/1997 | Newham |
| 5,654,694 A | 8/1997 | Newham |
| 5,699,038 A | 12/1997 | Ulrich et al. |
| 5,704,366 A | 1/1998 | Tacklind |
| 5,781,108 A | 7/1998 | Jacob et al. |
| 5,803,740 A | 9/1998 | Gesink et al. |
| 5,838,223 A | 11/1998 | Gallant et al. |
| 5,945,914 A | 8/1999 | Holmes et al. |
| 6,111,509 A | 8/2000 | Holmes |
| 6,292,102 B1 | 9/2001 | Smith |
| 6,297,738 B1 | 10/2001 | Newham |
| 6,307,476 B1 | 10/2001 | Smith et al. |
| 6,417,777 B2 | 7/2002 | Fitzgerald et al. |
| 6,441,742 B1 | 8/2002 | Lovely et al. |
| 6,544,200 B1 | 4/2003 | Smith et al. |
| 6,784,797 B2 | 8/2004 | Smith et al. |
| 6,791,460 B2 | 9/2004 | Dixon et al. |
| 6,897,781 B2 | 5/2005 | Cooper et al. |
| 6,934,986 B2 | 8/2005 | Krywiczanin et al. |
| 6,998,986 B2 | 2/2006 | Smith |
| 7,030,764 B2 | 4/2006 | Smith et al. |
| 7,078,676 B2 | 7/2006 | Smith et al. |
| 7,079,036 B2 | 7/2006 | Cooper et al. |
| 7,126,836 B2 | 10/2006 | Tanaka |
| 7,168,990 B2 | 1/2007 | Suzuki et al. |
| 7,209,044 B2 | 4/2007 | Reustle |
| 7,304,580 B2 | 12/2007 | Sullivan et al. |
| 7,319,400 B2 | 1/2008 | Smith et al. |
| 7,327,219 B2 | 2/2008 | Lederer, IV |
| 7,378,975 B1 | 5/2008 | Smith et al. |
| 7,453,365 B2 | 11/2008 | Reustle |
| 7,472,440 B2 | 1/2009 | Bartlett et al. |
| 7,521,963 B1 | 4/2009 | Xin-LeBlanc |
| 7,541,935 B2 | 6/2009 | Dring et al. |
| 7,570,152 B2 | 8/2009 | Smith et al. |
| 7,656,299 B2 | 2/2010 | Gentry et al. |
| 7,666,151 B2 | 2/2010 | Sullivan et al. |
| 7,698,765 B2 | 4/2010 | Bobey et al. |
| 7,746,218 B2 | 6/2010 | Collins, Jr. et al. |
| 7,830,385 B2 | 11/2010 | Kulas |
| 7,844,747 B2 | 11/2010 | Pedrazzini et al. |
| 7,849,545 B2 | 12/2010 | Flocard et al. |
| 7,852,208 B2 | 12/2010 | Collins, Jr. et al. |
| 7,868,740 B2 | 1/2011 | McNeely et al. |
| 7,916,036 B1 | 3/2011 | Pope et al. |
| 7,986,242 B2 | 7/2011 | Dixon et al. |
| 8,005,686 B2 | 8/2011 | Smith |
| 8,031,057 B2 | 10/2011 | McNeely et al. |
| 8,046,625 B2 | 10/2011 | Ferguson et al. |
| 8,068,027 B2 | 11/2011 | Auerbach et al. |
| 8,069,512 B2 | 12/2011 | Rawls-Meehan |
| 8,090,478 B2 | 1/2012 | Skinner et al. |
| 8,108,957 B2 | 2/2012 | Richards et al. |
| 8,120,471 B2 | 2/2012 | Collins, Jr. et al. |
| 8,146,191 B2 | 4/2012 | Bobey et al. |
| 8,154,413 B2 | 4/2012 | Dring et al. |
| 8,169,304 B2 | 5/2012 | Schuman, Sr. et al. |
| 8,199,150 B2 | 6/2012 | Kulas |
| 8,272,892 B2 | 9/2012 | McNeely et al. |
| 8,274,360 B2 | 9/2012 | Sampath et al. |
| 8,284,047 B2 | 10/2012 | Collins, Jr. et al. |
| 8,310,336 B2 | 11/2012 | Muhsin et al. |
| 8,322,810 B2 | 12/2012 | Silverbrook |
| 8,375,488 B2 | 2/2013 | Rawls-Meehan |
| 8,384,526 B2 | 2/2013 | Schuman, Sr. et al. |
| 8,392,747 B2 | 3/2013 | Ferguson et al. |
| 8,421,606 B2 | 4/2013 | Collins, Jr. et al. |
| 8,456,286 B2 | 6/2013 | Schuman et al. |
| 8,461,968 B2 | 6/2013 | Ball et al. |
| 8,483,848 B2 | 7/2013 | Langejurgen |
| 8,536,990 B2 | 9/2013 | Collins, Jr. et al. |
| 8,564,445 B2 | 10/2013 | Dring et al. |
| 8,565,934 B2 | 10/2013 | Rawls-Meehan |
| 8,584,279 B2 | 11/2013 | Richards et al. |
| 8,598,995 B2 | 12/2013 | Schuman et al. |
| 8,604,916 B2 | 12/2013 | McNeely et al. |
| 8,604,917 B2 | 12/2013 | Collins et al. |
| 8,620,477 B2 | 12/2013 | Skinner et al. |
| 8,674,996 B2 | 3/2014 | Kulas |
| 8,682,457 B2 | 3/2014 | Rawls-Meehan |
| 8,717,181 B2 | 5/2014 | Tallent et al. |
| 8,717,359 B2 | 5/2014 | Kulas |
| 8,730,009 B2 | 5/2014 | Barry |
| 8,762,766 B2 | 6/2014 | Ferguson et al. |
| 8,779,924 B2 | 7/2014 | Pesot et al. |
| 8,803,669 B2 | 8/2014 | Schuman, Sr. et al. |
| 8,823,529 B2 | 9/2014 | Reed, Jr. |
| 8,866,598 B2 | 10/2014 | Collins, Jr. et al. |
| 8,869,328 B2 | 10/2014 | Rawls-Meehan |
| 8,909,357 B2 | 12/2014 | Rawls-Meehan |
| 8,917,166 B2 | 12/2014 | Collins, Jr. et al. |
| 8,926,535 B2 | 1/2015 | Rawls-Meehan |
| 9,031,673 B2 | 5/2015 | Rawls-Meehan |
| 9,050,031 B2 | 6/2015 | Collins, Jr. et al. |
| 9,098,993 B2 | 8/2015 | Reed, Jr. |
| 9,107,511 B2 | 8/2015 | Skinner et al. |
| 9,128,474 B2 | 9/2015 | Rawls-Meehan |
| 9,142,117 B2 | 9/2015 | Muhsin et al. |
| 9,142,923 B2 | 9/2015 | McNeely et al. |
| 9,218,454 B2 | 12/2015 | Kiani et al. |
| 9,226,593 B2 | 1/2016 | Rawls-Meehan |
| 9,235,979 B2 | 1/2016 | Schuman, Sr. et al. |
| 9,237,814 B2 | 1/2016 | Rawls-Meehan |
| 9,295,338 B2 | 3/2016 | Rawls-Meehan |
| 9,299,242 B2 | 3/2016 | Schuman et al. |
| 9,323,894 B2 | 4/2016 | Kiani |
| 9,336,672 B2 | 5/2016 | Collins, Jr. et al. |
| 9,411,934 B2 | 8/2016 | Robinson et al. |
| 2003/0182158 A1 | 9/2003 | Son |
| 2003/0229730 A1 | 12/2003 | Pedrazzini et al. |
| 2004/0010849 A1 | 1/2004 | Krywiczanin et al. |
| 2004/0046668 A1 | 3/2004 | Smith et al. |
| 2004/0111045 A1 | 6/2004 | Sullivan et al. |
| 2004/0183681 A1 | 9/2004 | Smith |
| 2004/0245626 A1 | 12/2004 | Tanaka |
| 2004/0249673 A1 | 12/2004 | Smith |
| 2005/0011738 A1 | 1/2005 | Smith et al. |
| 2005/0046575 A1 | 3/2005 | Cooper et al. |
| 2005/0082466 A1 | 4/2005 | Smith et al. |
| 2005/0083207 A1 | 4/2005 | Smith et al. |
| 2005/0166324 A1 | 8/2005 | Dixon et al. |
| 2005/0171964 A1 | 8/2005 | Kulas |
| 2005/0172398 A1 | 8/2005 | Smith et al. |
| 2005/0179536 A1 | 8/2005 | Lederer |
| 2005/0185799 A1 | 8/2005 | Bertram |
| 2005/0190062 A1 | 9/2005 | Sullivan et al. |
| 2005/0275544 A1 | 12/2005 | Reustle |
| 2006/0020765 A1 | 1/2006 | Mahrla et al. |
| 2006/0264785 A1 | 11/2006 | Dring et al. |
| 2007/0225934 A1 | 9/2007 | Moriya et al. |
| 2008/0010747 A1 | 1/2008 | Dixon et al. |
| 2008/0030349 A1 | 2/2008 | Reustle |
| 2008/0115277 A1 | 5/2008 | Rawls-Meehan |
| 2008/0169931 A1 | 7/2008 | Gentry et al. |
| 2008/0291046 A1 | 11/2008 | Langejurgen |
| 2008/0308518 A1 | 12/2008 | Sprishen |
| 2008/0314900 A1 | 12/2008 | Biesecker et al. |
| 2009/0119330 A1 | 5/2009 | Sampath et al. |
| 2009/0184967 A1 | 7/2009 | Kulas |
| 2009/0189906 A1 | 7/2009 | Kulas |
| 2009/0189989 A1 | 7/2009 | Kulas |
| 2009/0266736 A1 | 10/2009 | Sprishen et al. |
| 2010/0057543 A1 | 3/2010 | Dring et al. |
| 2010/0122415 A1 | 5/2010 | Turner et al. |
| 2010/0245090 A1 | 9/2010 | Smith et al. |
| 2011/0032036 A1 | 2/2011 | Pedrazzini et al. |
| 2011/0156886 A1 | 6/2011 | Clinkscales et al. |
| 2011/0298585 A1 | 12/2011 | Barry |
| 2011/0302719 A1* | 12/2011 | Schwirian ............ A61B 5/1115 5/706 |
| 2012/0005832 A1 | 1/2012 | Turner et al. |

(56) References Cited

U.S. PATENT DOCUMENTS

2012/0137436 A1\* 6/2012 Andrienko ............. A61G 7/018
5/600
2013/0091631 A1\* 4/2013 Hayes .................... A61G 7/002
5/600
2013/0096936 A1 4/2013 Sampath et al.

\* cited by examiner

CUSTOMIZED BED EXIT WARNINGS TO MODIFY PATIENT BEHAVIOR

PRIORITY CLAIM

This application claims priority under 35 U.S.C. § 119(e) to U.S. Provisional Application No. 62/197,294, filed Jul. 27, 2015, which is expressly incorporated by reference herein.

BACKGROUND

The present disclosure is related to patient support apparatuses, and in particular to patient support apparatuses used to provide warnings to patients supported by the patient support apparatuses. More particularly, the present disclosure relates to patient support apparatuses used to provide warnings to patients to discourage the patients from exiting the patient support apparatuses.

Patients exiting patient support apparatuses without caregiver assistance may be at risk of falling and sustaining injuries as a result. For example, patients exiting patient support apparatuses while delirious or in a state of dementia may be particularly prone to falling. Additionally, patients exiting patient support apparatuses without caregiver assistance may be at risk of inadvertently removing tubes used to deliver medication to the patients or lines used to monitor biological activities of the patients.

Patient support apparatuses may provide warnings to patients to discourage the patients from exiting the patient support apparatuses. Such warnings may be limited in a variety of ways. In some cases, the warnings may not allow enough time for the caregivers to assist the patients before the patients exit the patient support apparatuses without assistance. In other cases, the warnings may fail to discourage the patients from exiting the patient support apparatuses without assistance. In other cases still, the warnings may take the form of alarms that embarrass and compromise the dignity of the patients.

SUMMARY

The present application discloses one or more of the features recited in the appended claims and/or the following features which, alone or in any combination, may comprise patentable subject matter:

According to one aspect of the present disclosure, a patient support apparatus comprises a frame, a sensor, and a controller. The frame and a support surface cooperate to support a patient. The sensor is coupled to one of the frame and the support surface, and the sensor is configured to provide an input signal indicative of a characteristic associated with the patient. The controller is coupled to the sensor, and the controller includes a processor and memory. The controller is configured to receive the input signal, associate the characteristic indicated by the input signal with patient information stored in an electronic medical records system, and cause a message customized to the patient according to the patient information to be issued to the patient.

In some embodiments, the characteristic may correspond to a position of the patient on the support surface. The message may comprise an audible message that addresses the patient by name and discourages the patient from exiting the support surface. Additionally, in other embodiments, the message may comprise a visual message that addresses the patient by name and discourages the patient from exiting the support surface.

In some embodiments, the patient support apparatus may further comprise a pendant coupled to the controller, and the controller may be configured to cause the message to be issued by the pendant. The controller may be configured to cause another message to be issued by the pendant to the patient to accompany the message issued by the pendant to the patient. One of the message and the another message may be an audible message, and the other of the message and the another message may be a visual message.

In some embodiments, the controller may be further configured to determine contact information for at least one family member of the patient based on the patient information and cause the at least one family member to be contacted using the contact information to inform the at least one family member of the characteristic. The controller may be configured to cause a text message to be sent to a mobile device of the at least one family member. Additionally, in other embodiments, the controller may be configured to cause the patient support apparatus to be connected to a mobile device of the at least one family member via a telephone line.

According to another aspect of the present disclosure, a patient support apparatus comprises a frame, a sensor, and a controller. The frame and a support surface cooperate to support a patient. The sensor is coupled to one of the frame and the support surface, and the sensor is configured to provide a first input signal indicative of a first characteristic associated with the patient. The controller is coupled to the sensor, and the controller includes a processor and memory. The controller is configured to receive the first input signal, associate the characteristic indicated by the first input signal with patient information stored in an electronic medical records system, and, if the controller receives a second input signal indicative of a second characteristic associated with the patient, cause a visual message customized to the patient according to the patient information to be issued to the patient in response to receiving the second input signal.

In some embodiments, the visual message may address the patient by name. The first characteristic may correspond to a position of the patient on the support surface. The second characteristic may correspond to one of a hard-of-hearing condition and a delirious condition of the patient.

In some embodiments, if the controller receives the second input signal, the controller may cause the visual message to be displayed to the patient on one of the following: a footboard coupled to the frame, siderails coupled to the frame, a floor supporting the patient support apparatus, a door permitting entry to a room in which the patient support apparatus is located, or a display positioned inside the room. If the controller does not receive the second input signal, the controller may be configured to cause an audible message customized to the patient according to the patient information to be issued to the patient.

According to yet another aspect of the present disclosure, a method of communicating a message to a patient by a patient support apparatus including a frame, a support surface supported by the frame, and a sensor configured to provide an input signal indicative of a characteristic associated with the patient comprises receiving the input signal, associating the characteristic indicated by the input signal with patient information stored in an electronic medical records system, and causing a message customized to the patient according to the patient information to be issued to the patient.

In some embodiments, the characteristic may correspond to a position of the patient on the support surface, and the message may address the patient by name and discourage the patient from exiting the support surface. Additionally, in other embodiments, the method may further comprise determining contact information for at least one family member of the patient based on the patient information, and causing the at least one family member to be contacted using the contact information to inform the at least one family member of the characteristic. In some embodiments, causing the at least one family member to be contacted may comprise either causing a text message to be sent to a mobile device of the at least one family member or causing the patient support apparatus to be connected to the mobile device of the at least one family member via a telephone line.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
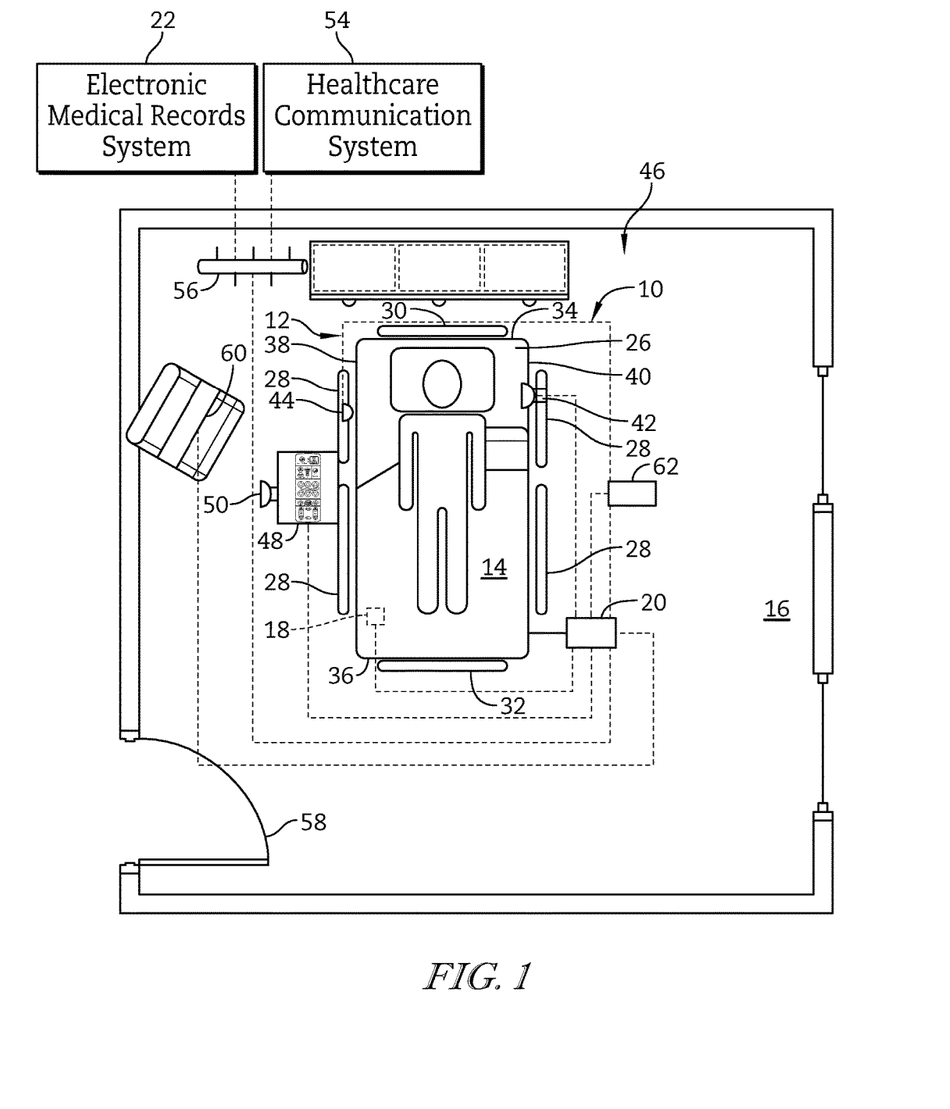
FIG. 1 is a top plan view of a patient support apparatus located in a patient's room of a hospital that includes a frame, a support surface cooperating with the frame to support a patient, a controller coupled to the frame, and a pendant coupled to the frame and the controller.

Referring now to FIG. 1, an illustrative patient support apparatus 10 is shown. The patient support apparatus 10 includes a frame 12 supported by wheels or casters and a support surface 14 that cooperates with the frame 12 to support a patient above a floor 16 on which the patient support apparatus 10 rests. The patient support apparatus 10 further includes a sensor 18 that is coupled to the frame 12. The sensor 18 is configured to provide an input signal indicative of a characteristic associated with the patient. The patient support apparatus 10 further includes a controller 20 that is coupled to the frame 12 and the sensor 18. The controller 20 is configured to receive the input signal, associate the characteristic with patient information stored in an electronic medical records system 22, and cause a message 24 customized to the patient according to the patient information to be issued to the patient.

Figure 7:
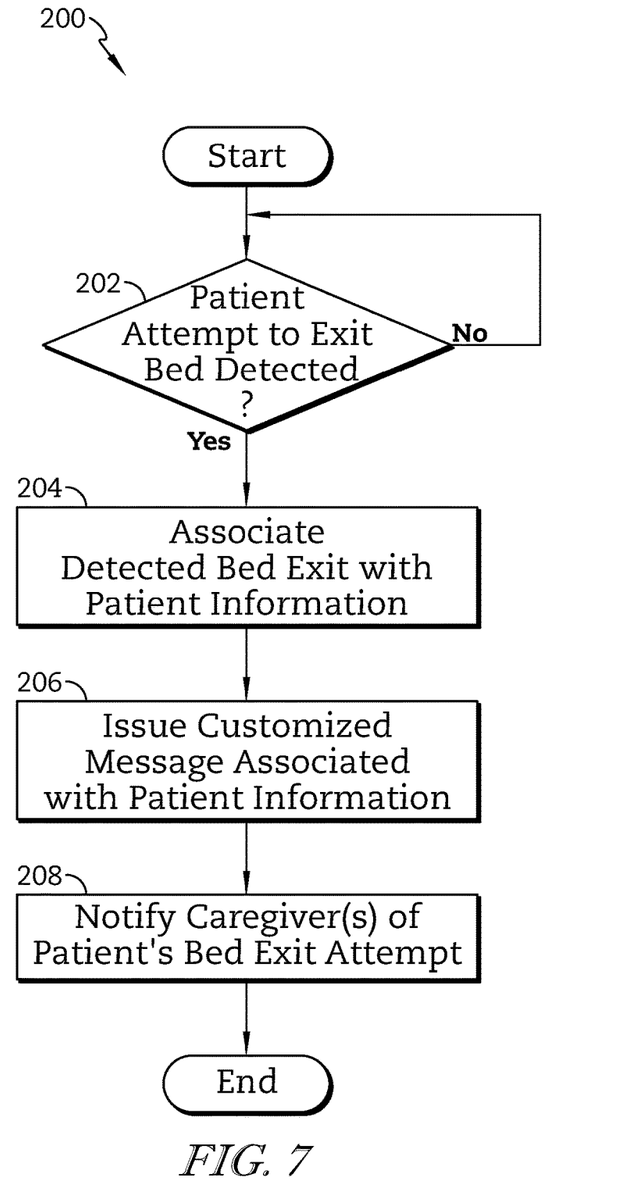
Figure 8:
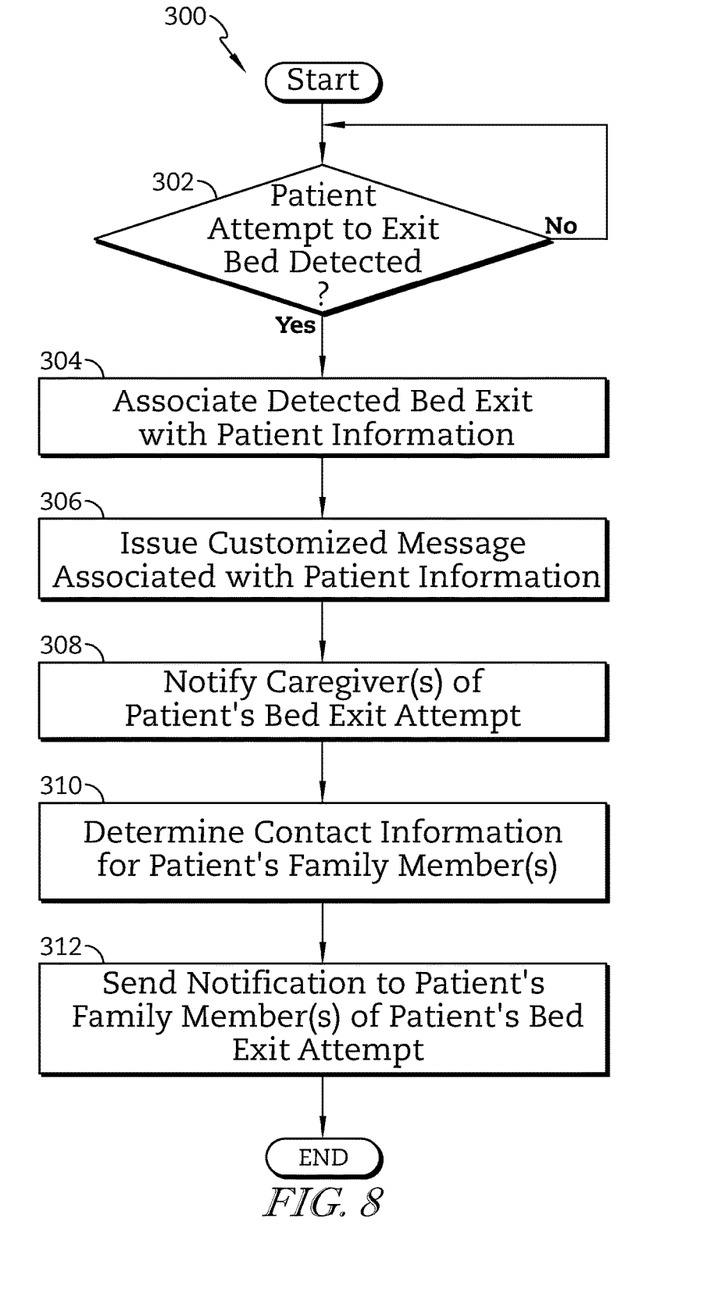
Figure 9:
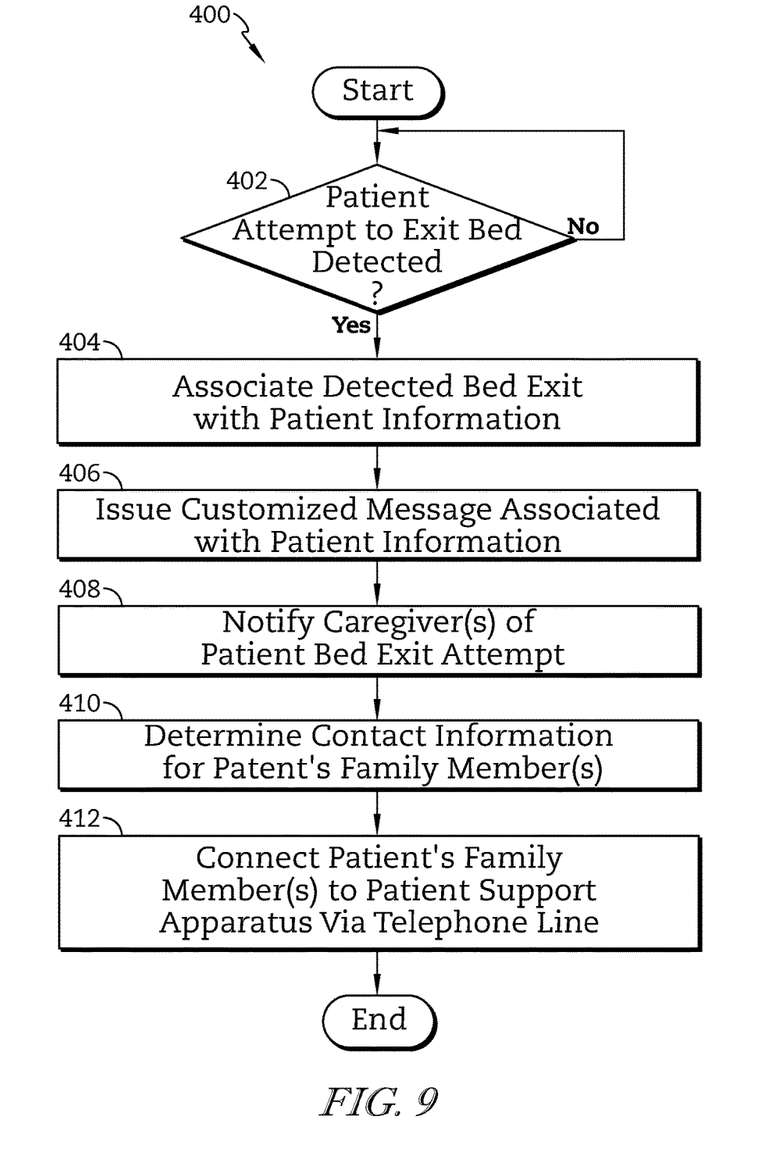

The characteristic indicated by the input signal provided by the sensor 18 illustratively corresponds to the position of the patient on the support surface 14. Specifically, the input signal provided by the sensor 18 may indicate that the patient is present and/or moving on the support surface 14, or that the patient has exited, or is in the process of exiting, the support surface 14. The controller 20 causes the message 24 to be issued to the patient in response to receiving the input signal from the sensor 18 indicating that the patient has exited, or is in the process of exiting, the support surface 14. As such, the customized message 24 represents an action performed by the patient support apparatus 10 in response to the detected exit of the patient from the support surface 14, as best seen in FIGS. 7-9.

The sensor 18 is illustratively embodied as a device or system configured to detect the patient's weight, or lack thereof, on the support surface 14 as suggested by FIG. 1. The sensor 18 may be embodied as, or otherwise include, one or more load cells. The sensor 18 may also be embodied as, or otherwise include, a patient positioning monitoring system.

The patient support apparatus 10 shown in FIG. 1 is illustratively embodied as a hospital bed. In other embodiments, however, the patient support apparatus 10 may be embodied as any one of a number of suitable patient support apparatuses. For example, the patient support apparatus 10 may be embodied as a recovery bed, a wheel chair, a surgical table, or the like.

The patient support apparatus 10 illustratively includes a mattress 26, a number of siderails 28, a headboard 30, and a footboard 32, each of which is supported by the frame 12 as shown in FIG. 1. The headboard 30 is positioned adjacent a head end 34 of the patient support apparatus 10. The footboard 32 is positioned adjacent a foot end 36 of the patient support apparatus 10 arranged opposite the head end 34. The siderails 28 extend between the head and foot ends 34, 36 along opposite sides 38, 40 of the patient support apparatus 10. The mattress 26 is positioned between the head and foot ends 34, 36 and between the sides 38, 40 of the patient support apparatus 10.

The patient support apparatus 10 also illustratively includes a microphone 42 and a speaker 44 each coupled to the frame 12 and the controller 20 as shown in FIG. 1. The microphone 42 is configured to provide an input signal in response to sound provided thereto. The speaker 44 is configured to provide sound in response to an input signal provided thereto. The microphone 42 may provide an input signal in response to sound provided thereto by the patient resting on the support surface 14 or a caregiver nearby the support surface 14. The speaker 44 may provide sound in response to an input signal provided thereto by a person located outside of a patient's room 46 of a hospital in which the patient support apparatus 10 is positioned.

The microphone 42 may be used to record the message 24 customized to the patient resting on the support surface 14, as described in greater detail below with reference to FIG. 6. The speaker 44 may be used to issue the message 24 to the patient when the patient's exit or attempted exit from the support surface 14 is detected by the sensor 18, as discussed below with reference to FIGS. 7-9.

The patient support apparatus 10 further illustratively includes a pendant 48 as shown in FIG. 1. The pendant 48 embodies a caregiver input-output device that is coupled to the controller 20. The pendant 48 is configured to communicate with the controller 20 when the pendant 48 is supported by the frame 12 or when the pendant 48 is physically separated from the frame 12 within the patient's room 46.

The pendant 48 may be used to issue the message 24 to the patient when the patient's exit or attempted exit from the support surface 14 is detected by the sensor 18, as discussed below with reference to FIG. 6. As such, the pendant 48 illustratively includes a pendant speaker 50 configured to issue the message 24 to the patient. The pendant 48 may also be used to issue another message 68 to the patient to accompany the message 24 when the patient's exit or attempted exit from the support surface 14 is detected by the sensor 18, as discussed below with reference to FIG. 2.

In addition to the pendant 48, the patient support apparatus 10 may further include other caregiver input-output devices capable of receiving and processing electrical input from a number of manually operable switches coupled to the caregiver input-output devices. The caregiver input-output devices may enable the caregiver to configure, activate, and deactivate certain electronically controlled functions of the patient support apparatus 10.

The patient support apparatus 10 may further include patient input-output devices capable of receiving and processing electrical input from a number of manually operable switches coupled to the patient input-output devices. The patient input-output devices may be used to enable the patient to activate and deactivate certain electronically controlled functions of the patient support apparatus 10 when the patient is positioned on the support surface 14. Such functions might include raising or lowering certain sections of the patient support apparatus 10, placing a call to a healthcare communication system 54 coupled to the controller 20 via a hospital network 56, or turning on various devices within the patient's room 46.

The patient support apparatus 10 is located in the patient's room 46 as shown in FIG. 1 and indicated above. The patient's room 46 illustratively includes the floor 16 and a door 58. The door 58 may be embodied as a door permitting or blocking access to the room 46. The door 58 may also be embodied as a door permitting or blocking access to a bathroom.

The patient's room 46 also illustratively includes a display 60 and a projector 62, each of which is coupled to the controller 20 as shown in FIG. 1. The display 60 may be used to issue the message 24 customized to the patient when the patient's exit or attempted exit from the support surface 14 is detected by the sensor 18, as discussed below with reference to FIG. 3. The projector 62 may be used to project the message 24 onto various objects within the patient's room 46 when the patient's exit or attempted exit from the support surface 14 is detected by the sensor 18, as discussed below with reference to FIG. 3.

Figure 2:
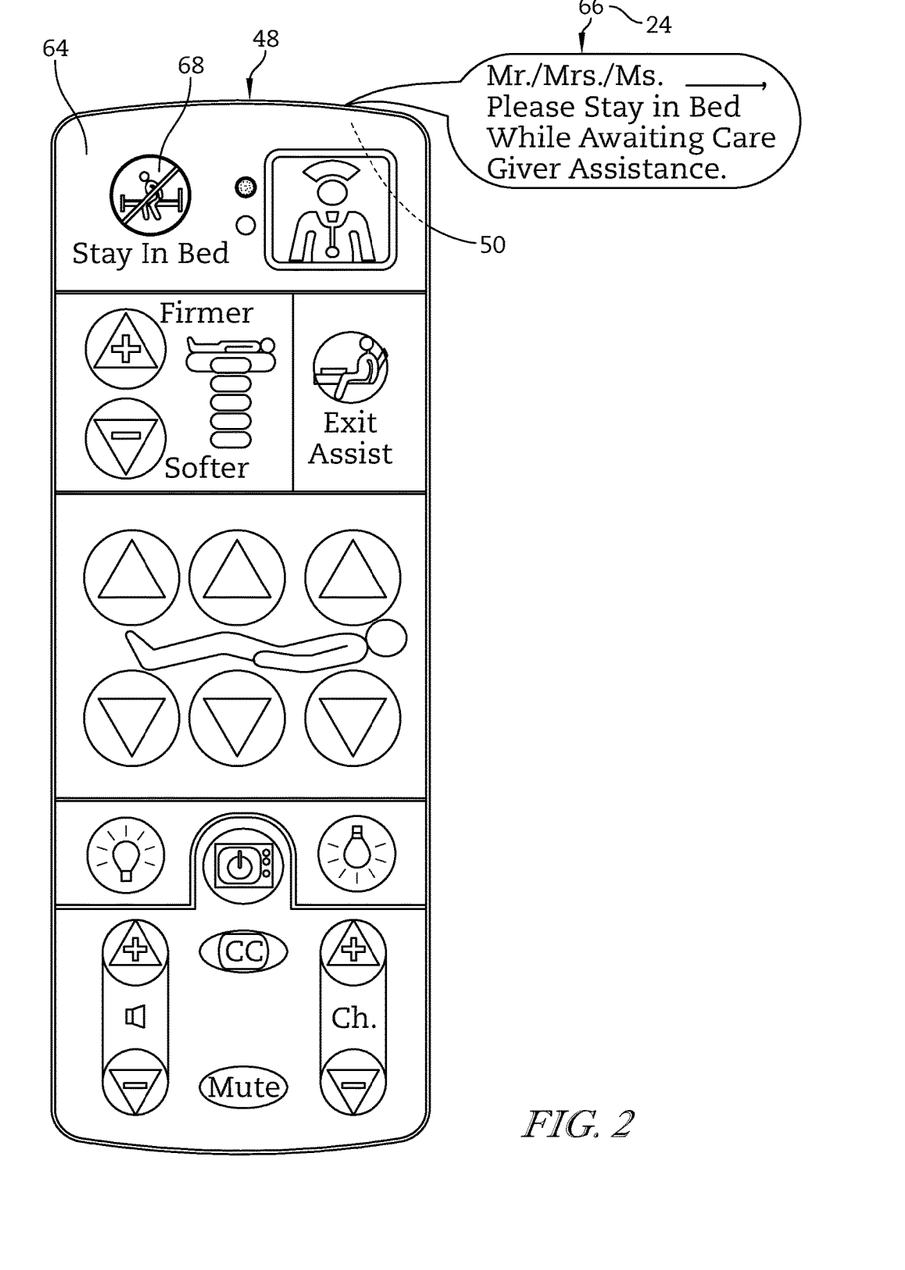
FIG. 2 is a detail view of the pendant of the patient support apparatus of FIG. 1 showing that the pendant is configured to issue an audible message customized to the patient to the patient to discourage the patient from exiting the support surface.

Referring now to FIG. 2, the illustrative pendant 48 is shown in detail. The pendant 48 is configured to issue an audible indication by the pendant speaker 50 to the patient when the patient's exit or attempted exit from the support surface 14 is detected by the sensor 18, as discussed below. In addition to the pendant speaker 50, the pendant 48 includes a touchscreen display 64. The touchscreen display 64 may include a graphical user interface enabling the caregiver to configure, activate, and deactivate certain of the electronically controlled functions of the patient support apparatus 10. The pendant 48 is configured to issue a visual indication by the touchscreen display 64 to the patient when the patient's exit or attempted exit from the support surface 14 is detected by the sensor 18, as discussed below.

The pendant 48 is configured to issue the message 24 to the patient when the patient's exit or attempted exit from the support surface 14 is detected by the sensor 18 as indicated above. As shown in FIG. 2, the message 24 issued by the pendant 48 is illustratively embodied as, or otherwise includes, an audible message 66 that is issued to the patient by the pendant speaker 50. The audible message 66 addresses the patient by name and discourages the patient from exiting the support surface 14 while awaiting assistance from a caregiver.

When the patient's exit or attempted exit from the support surface 14 is detected by the sensor 18, the pendant 48 is illustratively configured to issue another message 68 to the patient to accompany the message 66 as shown in FIG. 2. The message 68 is issued to the patient by the touchscreen display 64. The message 68 is embodied as, or otherwise includes, a visual message that discourages the patient from exiting the support surface 14.

Figure 3:
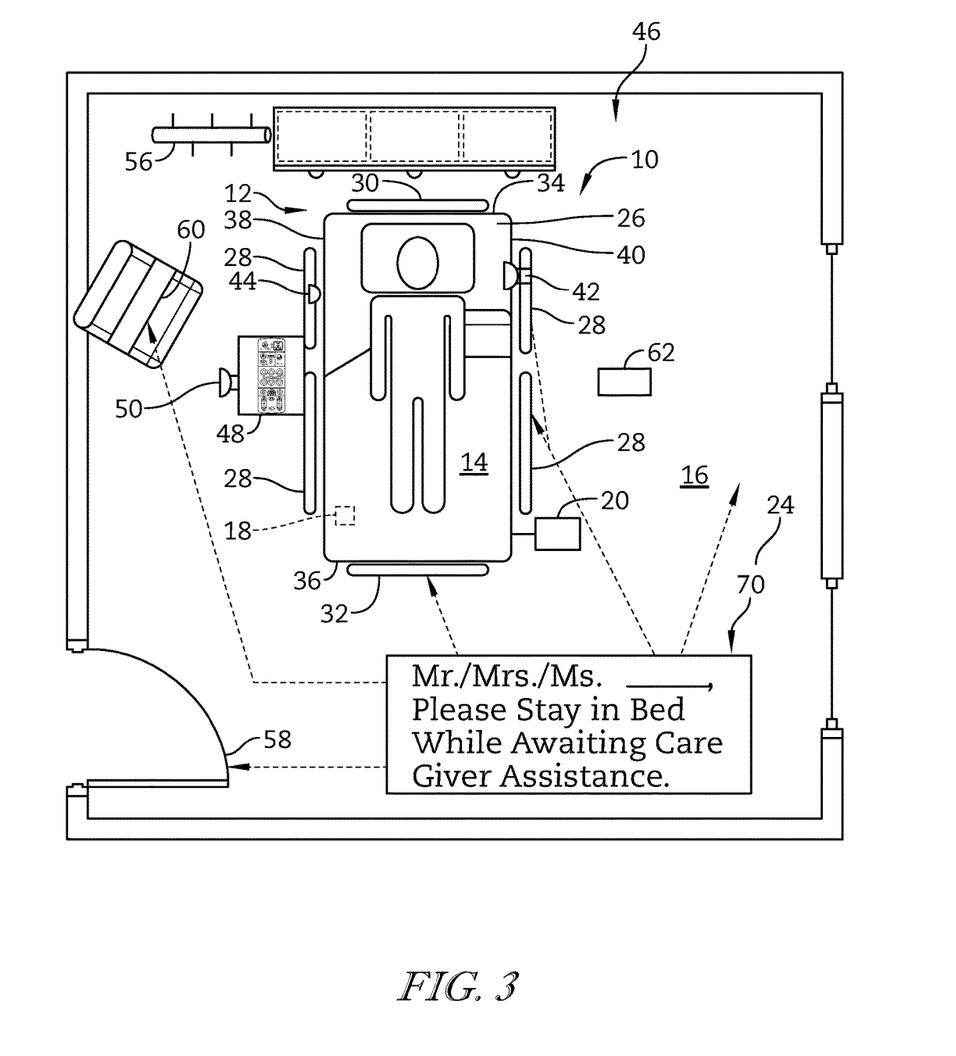
FIG. 3 is a top plan view of the patient support apparatus of FIG. 1 showing a visual message customized to the patient to discourage the patient from exiting the support surface displayed in one of a variety of locations on the patient support apparatus and in the patient room.

Referring now to FIG. 3, similar to FIG. 1, the patient's room 46 and the patient support apparatus 10 positioned within the patient's room 46 are shown. As shown in FIG. 3, the message 24 is illustratively embodied as, or otherwise includes, a visual message 70 that addresses the patient by name and discourages the patient from exiting the support surface 14 while awaiting assistance from a caregiver.

When the patient's exit or attempted exit from the support surface 14 is detected by the sensor 18, the controller 20 is configured to cause either the audible message 66 or the visual message 70 to be issued to the patient as shown in FIGS. 7-9. The circumstance under which each message 66, 70 is issued to the patient is discussed below with reference to FIGS. 7-9.

The visual message 70 may illustratively be issued to the patient by multiple devices in multiple locations within the patient's room 46 as shown in FIG. 3. In one example, the visual message 70 may be issued to the patient by the display 60. In another example, the visual message 70 may be issued to the patient by the projector 62 and projected onto the floor 16. In yet another example, the visual message 70 may be issued to the patient by the projector 62 and projected onto the door 58. In yet another example still, the visual message 70 may be issued to the patient by the projector 62 and projected onto the footboard 32. Finally, the visual message 70 may be issued to the patient by the projector 62 and projected onto the siderails 28. It should be appreciated that in other embodiments, the visual message 70 may be issued to the patient in other suitable locations by other suitable devices positioned in the patient's room 46.

Figure 4:
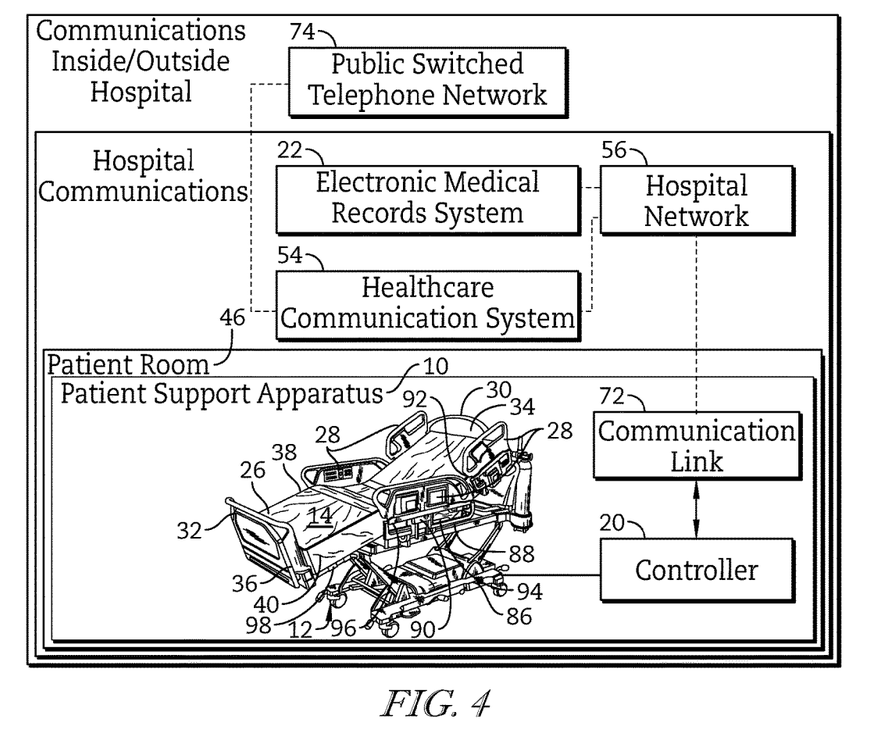
FIG. 4 is a diagrammatic view of the patient support apparatus of FIG. 1 showing a communication path between the controller and an electronic medical records system and between the controller and a public switched telephone network.

Referring now to FIG. 4, the illustrative frame 12 included in the patient support apparatus 10 is shown in detail. The frame 12 includes a lower frame 86, an upper frame 88, and a deck 90 coupled to the upper frame 88. The deck 90 is movable to a plurality of positions as suggested by FIG. 4. The deck 90 includes a head-deck section 92, a seat-deck section 94, a thigh-deck section 96, and a foot-deck section 98. The head-deck section 92 is mounted to the upper frame 88 to pivot about an axis relative to the seat-deck section 94 and to slide relative to the seat-deck section 94 and the upper frame 88 as described in U.S. Publication Nos. 2010/0122415 and 2012/0005832, which are incorporated herein in their entirety. The seat-deck section 94 is coupled to the upper frame 88 to move with the upper frame 88. The thigh-deck section 96 is coupled to the seat-deck section 94 to pivot relative to the seat-deck section 94. The foot-deck section 98 is coupled to the thigh-deck section 96 to pivot relative to the thigh-deck section 96. The foot-deck section 98 is also extendable and retractable to lengthen or shorten the deck 90 as desired by a caregiver or to accommodate repositioning of the deck 90.

Communication paths between the patient support apparatus 10 and systems/networks located inside the hospital and between the patient support apparatus 10 and system/ networks located outside the hospital are shown in FIG. 4. The patient support apparatus 10, specifically the controller 20, is illustratively coupled to the hospital network 56 through a communication link 72. The communication link 72 enables electrical communications originating at the patient support apparatus 10 (e.g., at the controller 20) to be communicated to the hospital network 56. In one example, the communication link 72 may be a wireless device enabling data to be exchanged between the controller 20 and the hospital network 56, such as a Bluetooth device. In another example, the communication link 72 may be a wired RS-232 connection permitting data to be exchanged between the controller 20 and the hospital network 56.

The hospital network 56 illustratively couples the controller 20 to the healthcare communication system 54 and to the electronic medical records system 22 of the hospital as shown in FIG. 4. The hospital network 56 may be embodied as, or otherwise include, a local area network, a wide area network, a secure enterprise cloud, secure portions of the Internet, and/or others. In some embodiments, in addition to the hospital network 56, intermediate devices and/or circuitry may enable the controller 20 to interface with the healthcare communication system 54 and with the electronic medical records system 22. For example, an input-output (I/O) board and a switch (e.g., a Power over Ethernet (POE) switch) may be used to communicatively couple the controller 20 to the healthcare communication system 54 and to the electronic medical records system 22.

The electronic medical records system 22 is illustratively used to store data for patients receiving care at the hospital as suggested by FIG. 4. Patient information such as the patient's name, an identifier for the patient support apparatus occupied by the patient, the patient's family members, and the family members' contact information, among other things, may be stored in an electronic history file (EHF) in a database included in the electronic medical records system 22. The messages 66, 70 customized to the patient resting on the support surface 14 may be stored in the electronic medical records system 22 within the patient's electronic history file, as discussed below with reference to FIG. 6.

The healthcare communication system 54 illustratively includes a nurse call system which may include a master station and a number of user stations. Each of the nurse call system user stations may include computers permitting caregiver access to patient information stored in the electronic medical records system 22 database. The nurse call system may also utilize server computers provided at the master station or the user stations to operate and manage certain functions of the nurse call system. For example, the server computers may receive and manage communications from devices connected to the nurse call system, control the placement, cancelling, and answering of nurse calls, and generate notifications/alerts prompting caregivers to assist patients.

The healthcare communication system 54 is coupled to a telecommunications server which acts as a gateway to the hospital's telecommunications infrastructure. The hospital's telecommunications infrastructure illustratively includes a network 74 that facilitates communication among a variety of telecommunication devices, including analog and digital devices, fixed telephones or mobile or cellular devices carried by hospital personnel or persons associated with patients receiving care at the hospital, personal data assistants (PDAs), pagers, and the like.

In the illustrative embodiment, the network 74 is embodied as, or otherwise includes, a public switched telephone network (PTSN) as shown in FIG. 4. In other embodiments, however, the network 74 may be embodied as, or otherwise include, other suitable networks, such as a private branch exchange (PBX), or the like. The public switched telephone network 74 is used to transmit communications originating at the patient support apparatus 10 (i.e., at the controller 20) to one or more mobile devices carried by one or more of the patient's family members who are located inside or outside of the hospital.

Figure 5:
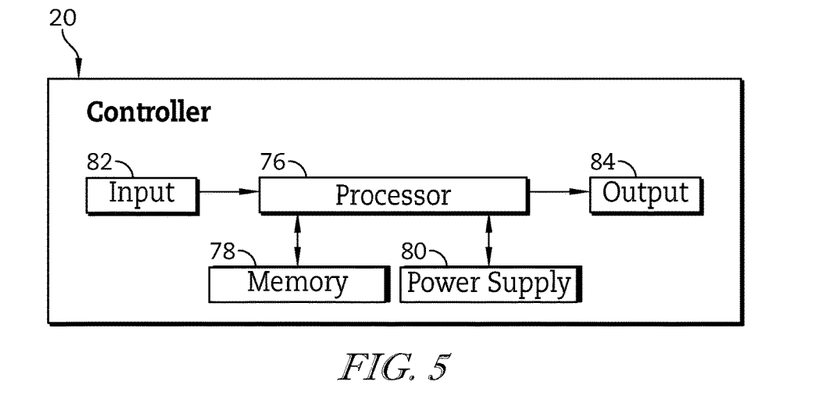
FIG. 5 is a diagrammatic view of the controller of the patient support apparatus of FIG. 4.

Referring now to FIG. 5, the illustrative controller 20 is shown in detail. The controller 20 manages a variety of electronically controlled functions associated with the patient support apparatus 10. The controller 20 includes a processor 76 and memory 78 coupled to the processor 76. The processor 76 receives power from a power supply 80. The memory 78 includes instructions that are executable by the processor 76 to cause the processor 76 to perform a variety of activities, as discussed below with reference to FIGS. 6-9.

The processor 76 is illustratively configured to receive input signals from one or more input devices 82 that are coupled to the controller 20 as shown in FIG. 5. The input devices 82 may include, for example, the sensor 18. The processor 76 is also illustratively configured to transmit output signals to one or more output devices 84 that are coupled to the controller 20. Such output devices 84 may include, for example, the pendant 48.

The controller 20 may be contained within a housing that is mountable to a fixed location on the patient support apparatus 10. For example, the housing may be mounted to the frame 12, as suggested by FIG. 4, or to the siderails 28, the footboard 32, or the headboard 30. The housing may contain electrical circuitry included with the controller 20 that is configured to interface with a network communicatively coupling the input and output devices 82, 84 to the processor 76, such as a bed network. The bed network may be an electronic network configured according to a CAN (Controller Area Network) or Echelon protocol, or any other suitable bed network communications protocol.

Figure 6:
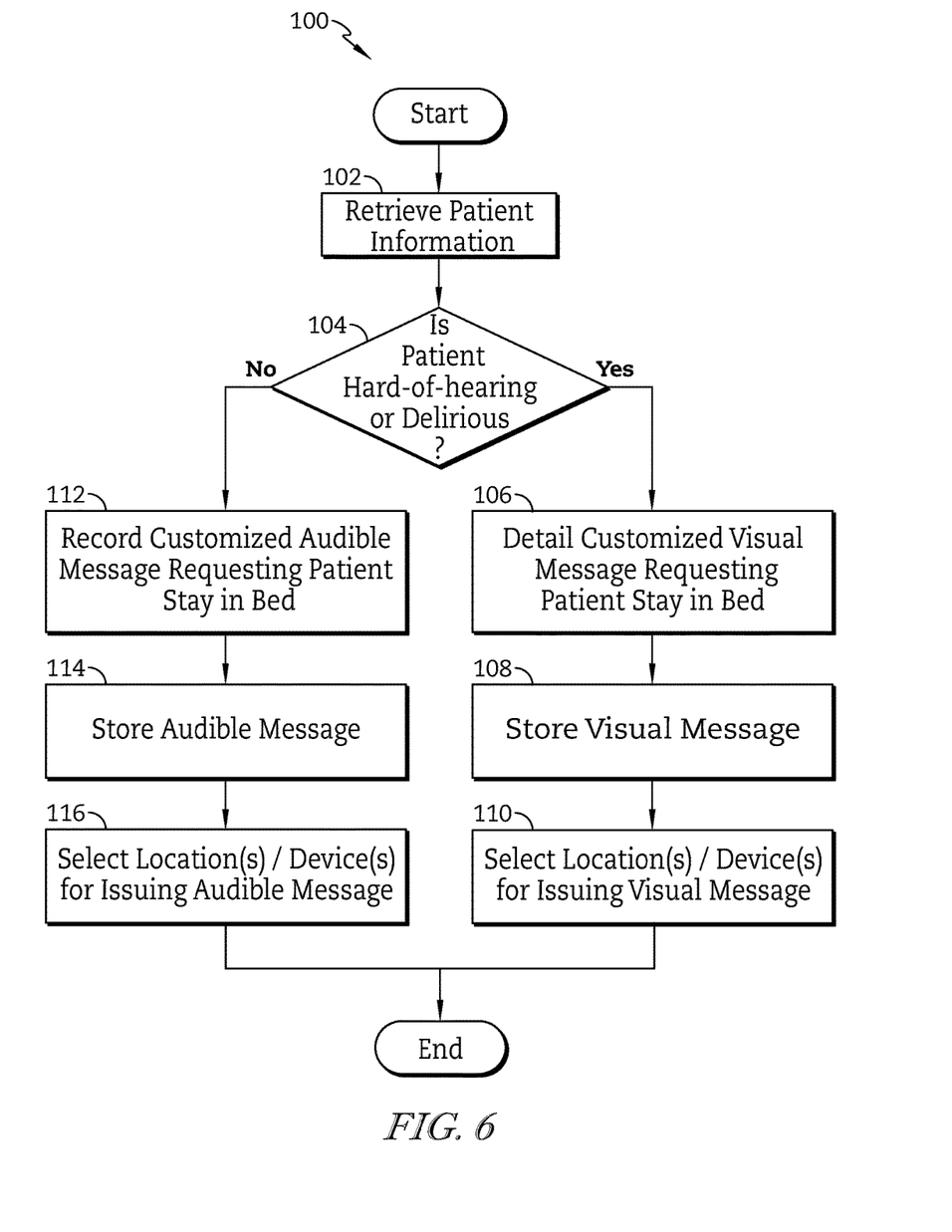
FIGS. 6-9 are diagrammatic views of sets of instructions executable by the controller of FIG. 5 to perform various activities.

Referring now to FIG. 6, an illustrative set of instructions 100 are shown that define a sequence of steps for specifying a characteristic of the patient and creating/storing either the audible message 66 or the visual message 70 based on the specified characteristic. The set of instructions 100 are stored in memory 78 of the controller 20. The instructions 100 direct the controller 20 to store either the audible message 66 or the visual message 70 so that the controller 20 may cause one of the messages 66, 70 to be issued when the patient's exit or attempted exit from the support surface 14 is detected by the sensor 18.

The set of instructions 100 illustratively includes a retrieve patient information step 102 that directs patient information for the patient occupying the support surface 14 to be retrieved as shown in FIG. 6. To do so, the controller 20, which is communicatively coupled to the electronic medical records system 22 through the communication link 72 and the hospital network 56, may retrieve the patient information from the electronic history file maintained for the patient in the database included in the system 22. The retrieve patient information step 102 may be initialized by a caregiver in response to a retrieve patient information prompt issued by the controller 20 to a caregiver input-output device coupled to the controller 20, such as the pendant 48 or a user interface, for example.

The set of instructions 100 next proceeds to a specify patient characteristic step 104 that directs the caregiver to specify the characteristic of the patient as shown in FIG. 6. The characteristic corresponds to one of a hard-of-hearing condition or a delirious condition of the patient. As such, the caregiver is directed in the specify patient characteristic step 104 to specify if the patient is either hard-of-hearing or delirious based on the patient information obtained in the patient information step 102. If the caregiver specifies that the patient is either hard-of-hearing or delirious, an input signal indicative of that characteristic is provided to the controller 20, and the instructions 100 next proceed to a detail visual message step 106. If the caregiver specifies that the patient is not hard-of-hearing or delirious, the instructions 100 next proceed to a record audible message step 112. The specify patient characteristic step 104 may be performed in response to a specify patient information prompt issued by the controller 20 to a caregiver input-output device coupled to the controller 20.

In response to the controller 20 receiving the input signal indicative of the characteristic in the specify patient characteristic step 104, the set of instructions 100 next proceeds to the detail visual message step 106 as shown in FIG. 6. In the detail visual message step 106, the caregiver is directed to detail the visual message 70 customized to the patient based on the patient information obtained in step 102. To do so, the caregiver may enter the visual message 70 on a caregiver input-output device coupled to the controller 20. The detail visual message step 106 may be performed in response to a detail visual message prompt issued by the controller 20 to a caregiver input-output device coupled to the controller 20.

The set of instructions 100 next proceeds to a store visual message step 108 that directs the visual message 70 detailed in the detail visual message step 106 to be stored as shown in FIG. 6. The visual message 70 may be stored in the electronic history file maintained for the patient in the electronic medical records system 22. The caregiver may direct the visual message 70 to be stored in the system 22 in response to a store visual message prompt issued by the controller 20 to a caregiver input-output device coupled to the controller 20.

The set of instructions 100 next proceeds to a select location/device for issuing visual message step 110 that directs the caregiver to select the location/device for issuing the visual message 70 detailed and stored in steps 106, 108 as shown in FIG. 6. The locations/devices for issuing the visual message 70 may be any one of those described above with reference to FIG. 3. The caregiver may select the device/location for issuing the visual message 70 in response to a select location/device for issuing visual message prompt issued by the controller 20 to a caregiver input-output device coupled to the controller 20. Following completion of the step 110, the set of instructions 100 are concluded.

Returning to step 104, if the caregiver specifies that the patient is not hard-of-hearing or delirious, the set of instructions 100 next proceeds to the record audible message step 112 as indicated above and shown in FIG. 6. In the record audible message step 112, the caregiver is directed to record the audible message 66 customized to the patient based on the patient information retrieved in step 102. To do so, the caregiver may record the audible message 66 using the microphone 42. The record audible message step 112 may be performed in response to a record audible message prompt issued by the controller 20 to a caregiver input-output device coupled to the controller 20.

The set of instructions 100 next proceeds to a store audible message step 114 that directs the audible message 66 recorded in the record audible message step 112 to be stored as shown in FIG. 6. The audible message 66 may be stored in the electronic history file maintained for the patient in the electronic medical records system 22. The caregiver may direct the audible message 66 to be stored in the system 22 in response to a store audible message prompt issued by the controller 20 to a caregiver input-output device coupled to the controller 20.

The set of instructions 100 next proceeds to a select location/device for issuing audible message step 116 that directs the caregiver to select the location/device for issuing the audible message 66 recorded and stored in steps 114, 116 as shown in FIG. 6. The locations/devices for issuing the audible message 66 may be any one of those described above with reference to FIG. 2. The caregiver may select the device/location for issuing the audible message 66 in response to a select location/device for issuing audible message prompt issued by the controller 20 to a caregiver input-output device coupled to the controller 20. Following completion of the step 116, the set of instructions 100 are concluded.

Referring now to FIG. 7, another illustrative set of instructions 200 are shown that define a sequence of steps for issuing one of the audible message 66 and the visual message 70 to the patient. The set of instructions 200 are stored in memory 78 of the controller 20. The set of instructions 200 direct the controller 20 to cause one of the messages 66, 70 to be issued to the patient when the patient's exit or attempted exit from the support surface 14 is detected by the sensor 18.

The set of instructions 200 include a detect bed exit step 202 that directs the controller 20 to determine whether the patient has exited or attempted to exit the support surface 14 as shown in FIG. 7. The controller 20 performs the detect bed exit step 202 based on the input signal provided to the controller 20 by the sensor 18. If the controller 20 determines that the patient has not exited or attempted to exit the support surface 14 based on the input signal provided by the sensor 18, the set of instructions 200 proceed no further. However, if the controller 20 determines that the patient has exited or attempted to exit the support surface 14 based on the input signal provided by the sensor 18, the set of instructions 200 proceed to an associate bed exit with patient information step 204.

The associate bed exit with patient information step 204 directs the controller 20 to associate the patient's detected exit or attempted exit from the patient support apparatus 10 with patient information for the patient as shown in FIG. 7. Essentially, the controller 20 performs step 204 by determining the identity of, and retrieving the message 24 customized to, the patient that has exited or attempted to exit the patient support apparatus 10. The input signal from the sensor 18 may signify, or otherwise be accompanied by, an identifier that identifies the patient support apparatus 10. After receiving the input signal, the controller 20 may communicate with the system 22 to match the identifier to the patient information for the patient identified by the system 22 as occupying the patient support apparatus 10. Once the controller 20 has matched the identifier with the patient information contained in the patient's electronic history file, the controller 20 may retrieve the message 24 customized to the patient.

The set of instructions 200 next proceeds to an issue message step 206 that directs the controller 20 to cause the message 24 to be issued to the patient according to the patient information as shown in FIG. 7. If the patient information does not indicate that the patient is hard-of-hearing or delirious, the controller 20 causes the audible message 66 recorded in step 112 to be issued to the patient at the device/location selected in step 116. If the patient information indicates that the patient is hard-of-hearing or delirious, the controller 20 causes the visual message 70 detailed in step 106 to be issued to the patient at the device/location selected in step 110.

The set of instructions 200 next proceeds to a notify caregiver(s) step 208 that directs the controller 20 to notify the caregiver(s) of the patient's exit or attempted exit from the patient support apparatus 10 as shown in FIG. 7. The controller 20 may generate an alert that is communicated to the nurse call system included in the healthcare communication system 54 to notify the appropriate caregiver(s) of the patient's exit or attempted exit from the patient support apparatus 10. After the caregiver(s) have been notified of the patient's exit or attempted exit from the patient support apparatus 10, the set of instructions 200 are concluded.

Referring now to FIG. 8, yet another illustrative set of instructions 300 are shown that define a sequence of steps for issuing one of the messages 66, 70 to the patient and thereafter contacting one or more family members of the patient. The set of instructions 300 may be stored in memory 78 of the controller 20. The set of instructions 300 directs the controller 20 to cause one of the messages 66, 70 to be issued to the patient when the patient's exit or attempted exit from the support surface 14 is detected by the sensor 18 and to thereafter cause the patient's family member(s) to be notified of the event.

The set of instructions 300 include a detect bed exit step 302 that directs the controller 20 to determine whether the patient has exited or attempted to exit the support surface 14 as shown in FIG. 8. The controller 20 performs the detect bed exit step 302 based on the input signal provided to the controller 20 by the sensor 18. If the controller 20 determines that the patient has not exited or attempted to exit the support surface 14 based on the input signal provided by the sensor 18, the set of instructions 300 proceed no further. However, if the controller determines that the patient has exited or attempted to exit the support surface 14 based on the input signal provided by the sensor 18, the set of instructions 300 proceed to an associate bed exit with patient information step 304.

The associate bed exit with patient information step 304 directs the controller 20 to associate the patient's detected exit or attempted exit of the patient support apparatus 10 with patient information for the patient as shown in FIG. 8. Essentially, the controller 20 performs step 304 by determining the identity of, and retrieving the message 24 customized to, the patient that has exited or attempted to exit the patient support apparatus 10. The input signal from the sensor 18 may signify, or otherwise be accompanied by, an identifier that identifies the patient support apparatus 10. After receiving the input signal, the controller 20 may communicate with the system 22 to match the identifier to the patient information for the patient identified by the system 22 as occupying the patient support apparatus 10. Once the controller 20 has matched the identifier with the patient information contained in the patient's electronic history file, the controller 20 may retrieve the message 24 customized to the patient.

The set of instructions 300 next proceeds to an issue message step 306 that directs the controller 20 to cause the message 24 to be issued according to the patient information as shown in FIG. 8. If the patient information does not indicate that the patient is hard-of-hearing or delirious, the controller 20 causes the audible message 66 recorded in step 112 to be issued to the patient at the device/location selected in step 116. If the patient information indicates that the patient is hard-of-hearing or delirious, the controller 20 causes the visual message 70 detailed in step 106 to be issued to the patient at the device/location selected in step 110.

The set of instructions 300 next proceeds to a notify caregiver(s) step 308 that directs the controller 20 to notify the caregiver(s) of the patient's exit or attempted exit from the patient support apparatus 10 as shown in FIG. 8. The controller 20 may generate an alert that is communicated to the nurse call system included in the healthcare communication system 54 to notify the appropriate caregiver(s) of the patient's exit or attempted exit from the patient support apparatus 10.

The set of instructions 300 next proceeds to a determine family member contact information step 310 that directs the controller 20 to determine contact information for one or more family members of the patient as shown in FIG. 8. To do so, the controller 20 communicates with the electronic medical records system 22 to access the family member contact information contained in the patient's electronic history file. The family member contact information is illustratively embodied as, or otherwise includes, information (e.g., telephone numbers) for communicating with one or more mobile devices carried by the patient's family members.

The set of instructions 300 next proceeds to a send family member notification step 312 that directs the controller 20 to contact the patient's one or more family members using the information determined in step 310 as shown in FIG. 8. The controller 20 communicates with the one or more mobile devices carried by the patient's family members through the communication link 72, the hospital network 56, the healthcare communication system 54, and the public switched telephone network 74. The controller 20 illustratively sends a text message to the mobile device(s) carried by the patient's one or more family members to inform them of the patient's exit or attempted exit from the patient support apparatus 10. In response to receiving the text message(s), the patient's one or more family member(s) may take action to further discourage the patient from exiting the patient support apparatus 10 while awaiting caregiver assistance. Upon completion of the send family member notification step 312, the set of instructions 300 are concluded.

Referring now to FIG. 9, yet another illustrative set of instructions 400 still are shown that define a sequence of steps for issuing one of the messages 66, 70 to the patient and thereafter contacting the patient's one or more family members. The set of instructions 400 may be stored in memory 78 of the controller 20. The set of instructions 400 directs the controller to cause one of the messages 66, 70 to be issued to the patient when the patient's exit or attempted exit from the support surface 14 is detected by the sensor 18 and to thereafter cause the patient's family member(s) to be notified of the event.

The set of instructions 400 includes a detect bed exit step 402 that directs the controller 20 to determine whether the patient has exited or attempted to exit the support surface 14 as shown in FIG. 9. The controller 20 performs the detect bed exit step 402 based on the input signal provided to the controller 20 by the sensor 18. If the controller 20 determines that the patient has not exited or attempted to exit the support surface 14 based on the input signal provided by the sensor 18, the set of instructions 400 proceed no further. However, if the controller determines that the patient has exited or attempted to exit the support surface 14 based on the input signal provided by the sensor 18, the set of instructions 400 proceed to an associate bed exit with patient information step 404.

The associate bed exit with patient information step 404 directs the controller 20 to associate the patient's detected exit or attempted exit from the patient support apparatus 10 with patient information for the patient as shown in FIG. 9. Essentially, the controller 20 performs step 404 by determining the identity of, and retrieving the message 24 customized to, the patient that has exited or attempted to exit the patient support apparatus 10. The input signal from the sensor 18 may signify, or otherwise be accompanied by, an identifier that identifies the patient support apparatus 10. After receiving the input signal, the controller 20 may communicate with the electronic medical records system 22 to match the identifier to the patient information for the patient identified by the system 22 as occupying the patient support apparatus 10. Once the controller 20 has matched the identifier with the patient information contained in the patient's electronic history file, the controller 20 may retrieve the message 24 customized to the patient.

The set of instructions 400 next proceeds to an issue message step 406 that directs the controller 20 to cause the message 24 to be issued according to the patient information as shown in FIG. 9. If the patient information does not indicate that the patient is hard-of-hearing or delirious, the controller 20 causes the audible message 66 recorded in step 112 to be issued to the patient at the device/location selected in step 116. If the patient information indicates that the patient is hard-of-hearing or delirious, the controller 20 causes the visual message 70 detailed in step 106 to be issued to the patient at the device/location selected in step 110.

The set of instructions 400 next proceeds to a notify caregiver(s) step 408 that directs the controller 20 to notify the caregiver(s) of the patient's exit or attempted exit from the patient support apparatus 10 as shown in FIG. 9. The controller 20 may generate an alert in step 408 that is communicated to the nurse call system included in the healthcare communication system 54 to notify the appropriate caregiver(s) of the patient's exit or attempted exit from the patient support apparatus 10.

The set of instructions 400 next proceeds to a determine family member contact information step 410 that directs the controller 20 to determine contact information for one or more family members of the patient as shown in FIG. 9. To do so, the controller 20 communicates with the electronic medical records system 22 to access the family member contact information contained in the patient's electronic history file. The family member contact information is illustratively embodied as, or otherwise includes, information (e.g., telephone numbers) for communicating with one or more mobile devices carried by the patient's family members.

The set of instructions 400 next proceeds to a connect family member(s) step 412 that directs the controller 20 to contact the patient's one or more family members using the information determined in step 410 as shown in FIG. 9. The controller 20 communicates with the one or more mobile devices carried by the patient's family members through the communications link 72, the hospital network 56, the healthcare communication system 54, and the public switched telephone network 74. The controller 20 illustratively connects the patient support apparatus 10 to the mobile device(s) carried by the patient's one or more family members via a telephone line to inform them of the patient's exit or attempted exit from the patient support apparatus 10. Through the telephone line, the patient's one or more family members may further discourage the patient from exiting the patient support apparatus 10 while awaiting caregiver assistance. Meanwhile, the patient may communicate with the one or more family members through the telephone line using, for example, the microphone 42 and the speaker 44 included in the patient support apparatus 10. Upon completion of the connect family member(s) step 412, the set of instructions 400 are concluded.

Although certain illustrative embodiments have been described in detail above, variations and modifications exist within the scope and spirit of this disclosure as described and as defined in the following claims.

The invention claimed is:

1. A patient support apparatus comprising
a frame and a support surface cooperating with the frame to support a patient,
a sensor coupled to one of the frame and the support surface, the sensor configured to provide an input signal indicative of a characteristic associated with the patient, and
a controller coupled to the sensor and including a processor and a memory device, the memory device including instructions that, when executed by the processor, cause the controller to receive the input signal, associate the characteristic indicated by the input signal with patient information stored in an electronic medical records system, and cause a message customized to the patient according to the patient information to be issued to the patient,
wherein the controller is further configured to determine contact information for at least one family member of the patient based on the patient information and cause the at least one family member to be contacted using the contact information to inform the at least one family member of the characteristic.

2. The patient support apparatus of claim 1, wherein the characteristic corresponds to a position of the patient on the support surface.

3. The patient support apparatus of claim 2, wherein the message comprises an audible message that addresses the patient by name and discourages the patient from exiting the support surface.

4. The patient support apparatus of claim 2, wherein the message comprises a visual message that addresses the patient by name and discourages the patient from exiting the support surface.

5. The patient support apparatus of claim 1, further comprising a pendant coupled to the controller, wherein the controller is configured to cause the message to be issued to the patient by the pendant.

6. The patient support apparatus of claim 5, wherein the controller is configured to cause another message to be issued by the pendant to the patient to accompany the message issued by the pendant to the patient.

7. The patient support apparatus of claim 6, wherein one of the message and the another message is an audible message, and the other of the message and the another message is a visual message.

8. The patient support apparatus of claim 1, wherein the controller is configured to cause the patient support apparatus to be connected to a mobile device of the at least one family member via a telephone line.

9. The patient support apparatus of claim 1, wherein the controller is configured to cause a text message to be sent to a mobile device of the at least one family member.

10. A patient support apparatus comprising
a frame and a support surface cooperating with the frame to support a patient,
a sensor coupled to one of the frame and the support surface, the sensor configured to provide a first input signal indicative of a first characteristic associated with the patient, and
a controller coupled to the sensor and including a processor and memory, the memory device including instructions that, when executed by the processor, cause the controller to receive the first input signal, associate the characteristic indicated by the first input signal with patient information stored in an electronic medical records system, and, if the controller receives a second input signal indicative of a second characteristic associated with the patient, cause a visual message customized to the patient according to the patient information to be issued to the patient in response to receiving the second input signal.

11. The patient support apparatus of claim 10, wherein the visual message addresses the patient by name.

12. The patient support apparatus of claim 11, wherein the first characteristic corresponds to a position of the patient on the support surface.

13. The patient support apparatus of claim 12, wherein the second characteristic corresponds to one of a hard-of-hearing condition and a dementia condition of the patient.

14. The patient support apparatus of claim 10, wherein if the controller receives the second input signal, the controller is configured to cause the visual message to be displayed to the patient on one of the following: a footboard coupled to the frame, siderails coupled to the frame, a floor supporting the patient support apparatus, a door of a room in which the patient support apparatus is located, or a display positioned inside the room.

15. The patient support apparatus of claim 14, wherein if the controller does not receive the second input signal, the controller is configured to cause an audible message customized to the patient according to the patient information to be issued to the patient.

16. A method of communicating a message to a patient by a patient support apparatus including a frame, a support surface supported by the frame, and a sensor configured to provide an input signal indicative of a characteristic associated with the patient, the method comprising
receiving the input signal,
associating the characteristic indicated by the input signal with patient information stored in an electronic medical records system,
causing a message customized to the patient according to the patient information to be issued to the patient, and
determining contact information for at least one family member of the patient based on the patient information, and causing the at least one family member to be contacted using the contact information to inform the at least one family member of the characteristic.

17. The method of claim 16, wherein causing the at least one family member to be contacted comprises either causing a text message to be sent to a mobile device of the at least one family member or causing the patient support apparatus to be connected to the mobile device of the at least one family member via a telephone line.

18. The method of claim 16, wherein the characteristic corresponds to a position of the patient on the support surface, and the message addresses the patient by name and discourages the patient from exiting the support surface.

* * * * *